(12) United States Patent
Lee et al.

(10) Patent No.: US 10,980,466 B2
(45) Date of Patent: Apr. 20, 2021

(54) BRAIN COMPUTER INTERFACE (BCI) APPARATUS AND METHOD OF GENERATING CONTROL SIGNAL BY BCI APPARATUS

(71) Applicant: Korea University Research and Business Foundation, Seoul (KR)

(72) Inventors: Seong-Whan Lee, Seoul (KR); Ji-Hoon Jeong, Seoul (KR); Keun-Tae Kim, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 342 days.

(21) Appl. No.: 16/124,419

(22) Filed: Sep. 7, 2018

(65) Prior Publication Data
US 2019/0073030 A1  Mar. 7, 2019

(30) Foreign Application Priority Data
Sep. 7, 2017 (KR) .......................... 10-2017-0114617

(51) Int. Cl.
*G06F 3/01* (2006.01)
*B25J 9/16* (2006.01)
(Continued)

(52) U.S. Cl.
CPC .............. *A61B 5/375* (2021.01); *A61B 5/369* (2021.01); *A61B 5/7264* (2013.01); *B25J 9/161* (2013.01);
(Continued)

(58) Field of Classification Search
CPC ... A61B 5/0482; A61B 5/0476; A61B 5/7275; A61B 5/7264; G06F 3/015; B25J 9/161; B25J 9/1612; B25J 9/1689; B25J 13/087
See application file for complete search history.

(56) References Cited

U.S. PATENT DOCUMENTS

2016/0235323 A1* 8/2016 Tadi ..................... A61B 5/0077

FOREIGN PATENT DOCUMENTS

KR         10-1205892 B1   11/2012

* cited by examiner

*Primary Examiner* — Christine H Matthews
*Assistant Examiner* — Joshua Daryl D Lannu
(74) *Attorney, Agent, or Firm* — NSIP Law

(57) ABSTRACT

The present disclosure provides a method of generating a control signal to control a motion of a robot arm device by a brain-computer interface (BCI) apparatus and the BCI apparatus. The present method includes: measuring a first electroencephalogram (EEG) and extracting an abstract feature of the first EEG; determining one of a reaching control mode, a hand grasp/opening control mode, and a wrist rotation control mode based on the abstract feature of the first EEG; performing feedback of the determined control mode to a user; measuring an error-related potential as a second EEG; redetermining the control mode by re-extracting an abstract feature of the first EEG when the error-related potential exceeds a threshold value or measuring a third EEG when the error-related potential does not exceed the threshold value; extracting a result value by applying different feature extraction methods and different classification methods to the third EEG depending on the determined control mode; and supplying a control signal generated based on the result value to the robot arm device.

6 Claims, 5 Drawing Sheets

(51) Int. Cl.
*A61B 5/375* (2021.01)
*A61B 5/00* (2006.01)
*B25J 13/08* (2006.01)
*A61B 5/369* (2021.01)

(52) U.S. Cl.
CPC ............ *B25J 9/1612* (2013.01); *B25J 9/1689* (2013.01); *B25J 13/087* (2013.01); *G06F 3/015* (2013.01); *A61B 5/7275* (2013.01)

BRAIN COMPUTER INTERFACE (BCI) APPARATUS AND METHOD OF GENERATING CONTROL SIGNAL BY BCI APPARATUS

CROSS-REFERENCE TO RELATED APPLICATION

This application claims the benefit under 35 USC 119(a) of Korean Patent Application No. 10-2017-0114617 filed on Sep. 7, 2017 in the Korean Intellectual Property Office, the entire disclosures of which are incorporated herein by reference for all purposes.

TECHNICAL FIELD

The present disclosure relates to a brain-computer interface (BCI) apparatus capable of more accurately generating a control signal to control a motion of a subject and a method of generating a control signal by the BO apparatus.

BACKGROUND

In general, brain waves can be classified into various types depending on their temporal feature, frequency band feature, and spatial feature are classified as follows. That is, the brain waves are classified into an alpha wave (frequency of 8 Hz to 13 Hz, amplitude of 20 V to 60 V) generated during relaxation with eyes closed, a beta wave (frequency of 14 Hz to 30 Hz, amplitude of 2 V to 20 V) generated during conscious concentration, a theta wave (frequency of 4 Hz to 7 Hz, amplitude of 20 V to 100 V) generated during light sleep, and the like. Notably, a Mu-band wave (8 Hz to 12 Hz) generated from the motor cortex of the brain during motor intention (or motor imagery) can be classified separately from the alpha wave.

A non-invasive brain-computer interface (BCI) refers to a technology capable of measuring and analyzing a user's brain waves without a separate surgical operation and thus controlling various external devices. A BCI apparatus can analyze brainwaves in a specific pattern generated intentionally just by thinking and thus control external devices. Such a BCI apparatus has been used to control prosthetic devices for disabled people who are not free to move their bodies due to severe disabilities such as Lou Gehrig's disease or spinal cord injury and used in medical field applications such as word spellers for communication.

Recently, BCI technology has been applied in various fields through the development of daily assistance services for people. In order to apply the BCI technology to daily life, an apparatus using the BCI technology needs to process various commands. However, conventional apparatuses using the BCI technology have been used only to detect and process a specific motor imagery. Therefore, the BCI technology has been limited in application to daily life.

In this regard, Korean Patent No. 10-1205892 (entitled "Analysis method of user intention recognition for brain-computer interface) discloses a method including: obtaining and converting brainwave data of a user into a frequency signal and then classifying a frequency domain related to motor sensation depending on a band of the converted frequency signal; detecting the user's intention recognition by analyzing features depending on the user's motor imagery; and displaying the result of detection of intention recognition to be seen by the user. However, this method is still limited to detecting and processing various motor imageries.

DISCLOSURE OF THE INVENTION

Problems to be Solved by the Invention

In view of the foregoing, the present disclosure provides a BCI apparatus capable of more efficiently and accurately controlling various motions of a subject such as a robot arm device linked to the BCI apparatus and a method of generating a control signal by the BCI apparatus.

However, problems to be solved by the present disclosure are not limited to the above-described problems. There may be other problems to be solved by the present disclosure.

Means for Solving the Problems

According to a first aspect of the present disclosure, a method of generating a control signal to control a subject by a brain-computer interface (BCI) apparatus, comprising: measuring a first electroencephalogram (EEG) and extracting an abstract feature of the first EEG, determining one control mode of at least one control mode to control a motion of the subject based on the abstract feature of the first EEG, performing feedback of the determined control mode to a user, measuring an error-related potential as a second EEG, redetermining the control mode by re-extracting an abstract feature of the first EEG when the error-related potential exceeds a threshold value or measuring a third EEG when the error-related potential does not exceed the threshold value, extracting a result value by applying different feature extraction methods and different classification methods to the third EEG depending on the determined control mode, and supplying a control signal generated based on the result value to the subject.

According to a second aspect of the present disclosure, a brain-computer interface (BCI) apparatus, comprising: an electroencephalogram (EEG) measurement device that measures an EEG; a memory that stores a program with which the BCI apparatus generates a control signal to control a motion of a subject linked to the BCI apparatus; and a control unit that executes the program stored in the memory, wherein upon execution of the program, the control unit extracts an abstract feature of a first EEG based on the first EEG measured by the EEG measurement device, determines one control mode of at least one control mode to control the motion of the subject based on the abstract feature, and the control unit performs feedback of the determined control mode to a user and compares an error-related potential measured as a second EEG by the EEG measurement device with a threshold value, and the control unit redetermines the control mode by remeasuring the first EEG when the error-related potential exceeds the threshold value, or the control unit extracts a result value by applying different feature extraction methods and different classification methods to a third EEG measured by the EEG measurement device depending on the determined control mode when the error-related potential does not exceed the threshold value, and supplies a control signal generated based on the result value to the subject.

According to a third aspect of the present disclosure, a computer-readable storage medium stores a program configured to implement a method of the first aspect on a computer.

Effects of the invention according to the present disclosure, it is possible to provide a method capable of more accurately generating a control signal to control a motion of a subject including a robot arm device according to a user's motor imagery and a BCI apparatus performing the method.

Notably, according to the present disclosure, it is possible to suppress the robot arm device from making a motion unintended by the user by rapidly determining a control mode using an abstract feature and performing feedback of the control mode to the user to check whether it matches with the user's motor imagery (or motor intention). Further, according to the present disclosure, a process of determining a control mode is performed separately from a process of actually controlling the robot arm device, and, thus, it is possible to control the robot arm device for each control mode more precisely.

DETAILED DESCRIPTION

Figure 1:
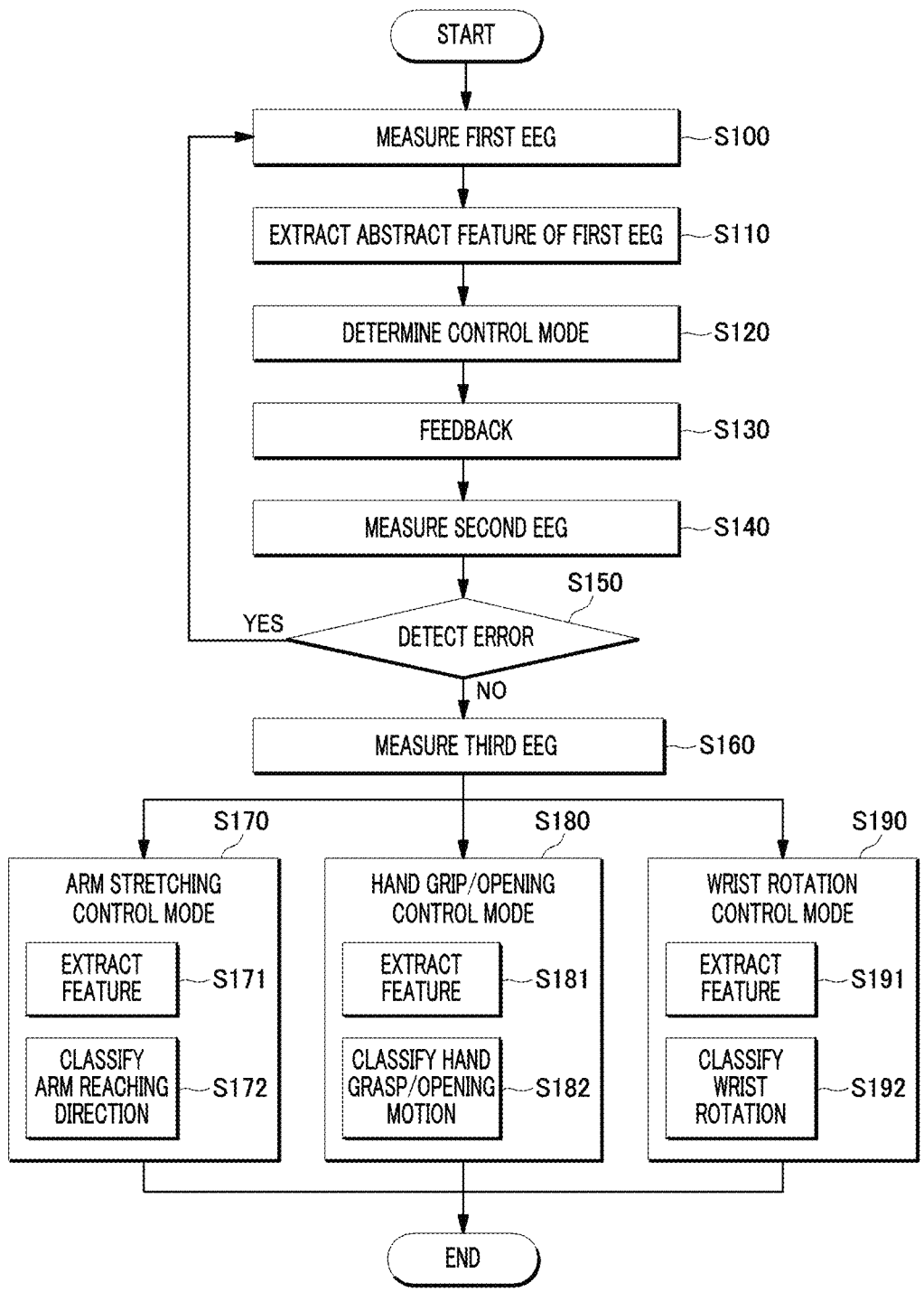
FIG. 1 is a flowchart showing a method of generating a control signal by a brain-computer interface (BCI) apparatus in accordance with various embodiments described herein.

Hereinafter, embodiments of the present disclosure will be described in detail with reference to the accompanying drawings so that those skilled in the art may readily implement the present disclosure. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Further, the term "motor imagery" used herein may also be referred to as motion imagery, motor intention, dynamic imagery, or the like.

Hereinafter, an embodiment of the present disclosure will be described in detail with reference to the accompanying drawings.

Figure 5:
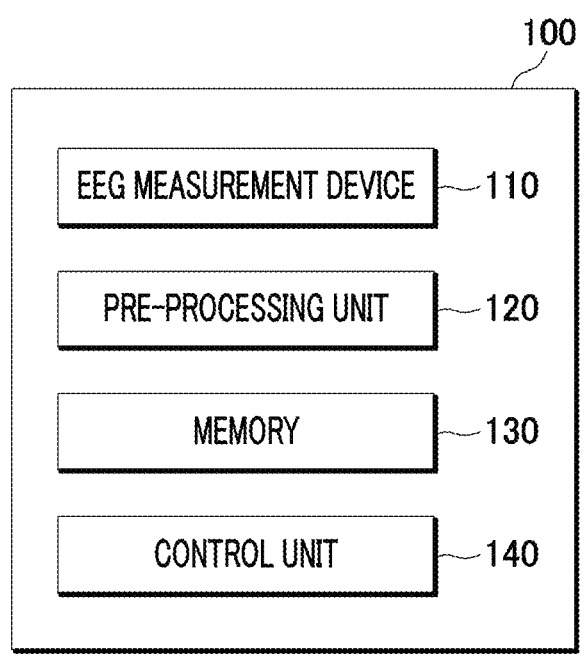
FIG. 5 illustrates a configuration of a BCI apparatus in accordance with various embodiments described herein.

FIG. 1 is a flowchart showing a method of generating a control signal by a brain-computer interface (BCI) apparatus in accordance with an embodiment of the present disclosure. Herein, a BCI apparatus 100 is illustrated in FIG. 5 and can be implemented as a computer or a portable device. Further, the BCI apparatus 100 can also be implemented as a wearable device that can be worn by a user. Furthermore, the BCI apparatus 100 may be configured as a unit integrated with a subject which moves in linkage with the BCI apparatus 100. Herein, the subject 100 may be a robot arm device (not illustrated) configured to assist an upper limb movement (i.e., arm movement) of the user, but may not be limited thereto. Herein, the robot arm device (not illustrated) may be configured to be wearable on the user's upper limb, but may not be limited thereto. The robot arm device may be provided separately from the user and configured to be movable according to the user's motor imagery.

Firstly, the BCI apparatus 100 measures a first EEG to determine a control mode for the user (S100). If the user inducibly or voluntarily performs a motor imagery to imagine his/her upper limb movement, the BCI apparatus 100 according to an embodiment of the present disclosure can detect an event-related desynchronization (ERD) signal/an event-related synchronization (ERS) signal generated in multiple regions of the brain (e.g., multiple regions in the sensorimotor cortex). Herein, the ERD signal is caused by a temporary decrease in the EEG at a specific frequency (e.g., Mu-band wave) in response to a stimulus (i.e., inducible/voluntary motor imagery), and the ERS signal is caused by an increase in the EEG at a specific frequency (e.g., beta wave) in response to a stimulus.

Particularly, while the user performs the motor imagery, the ERD signal is first generated, and after the motor imagery, the ERS signal is generated. Therefore, the first EEG measured by the BCI apparatus 100 to determine a control mode for the user may be an ERD signal generated first according to the user's motor imagery or an ERD/ERS signal.

Then, the BCI apparatus 100 extracts an abstract feature of the first EEG (S110). Herein, the abstract feature may be an abstract value as at least one of a frequency feature and a spatiotemporal feature based on an ERD pattern of the first EEG. For example, the BCI apparatus 100 may extract at least one of a frequency feature and a spatiotemporal feature based on the ERD signal and convert the extracted feature into a scalar value.

The frequency feature is shown in a frequency band depending on a motor imagery and may be a power (dB/Hz) variance for each frequency band of the ERD signal and can be abstracted as a maximum power value. To be specific, the BCI apparatus 100 may perform frequency filtering of the measured first EEG in a frequency band of from about 1 Hz to about 50 Hz, analyze a power variance for each frequency band, and extract a maximum power value. Further, the spatiotemporal feature may be an amplitude variance in a time-frequency domain of the ERD signal and can be abstracted as a frequency region in which a maximum amplitude appears. For example, the BCI apparatus 100 may convert the ERD signal into a frequency signal and average amplitude of the frequency signal in the direction of time to extract a spatiotemporal feature, and may also extract a frequency region in which spatiotemporal features are concentrated. Herein, the spatiotemporal feature can be extracted by a common spatial pattern method and the spatiotemporal feature-concentrated frequency region can be obtained with an already trained classifier.

Meanwhile, if the BCI apparatus 100 is involved in the user's left and right hand movements, the BCI apparatus 100 may determine control for the user's left hand or right hand based on the extracted feature. That is, if the user performs a motor imagery to imagine his/her left hand movement, an ERD signal is generated from the right hemisphere of his/her brain, and if the user performs a motor imagery to imagine his/her right hand movement, an ERD signal is generated from the left hemisphere of his/her brain. Therefore, the BCI apparatus 100 can determine a hand (i.e., left hand or right hand) corresponding to a motor imagery based on a brain region corresponding to the extracted feature.

Then, the BCI apparatus 100 determines a control mode based on the abstract feature of the first EEG (S120). Herein, the control mode is involved in generating a control signal to control a motion of the robot arm device (not illustrated) controlled by the BCI apparatus 100. For example, the control mode may include an reaching control mode, a hand grasp/opening control mode, and a wrist rotation control mode. In the respective control modes, the BCI apparatus 100 generates control signals to instruct the robot arm device (not illustrated) to make an reaching motion, a hand grasp/opening motion and a rotation motion.

Meanwhile, during the upper limb movement, the EEG shows a different feature variance for each of an reaching motion, a hand grasp/opening motion, and a wrist rotation motion. Therefore, the BCI apparatus 100 determines a control mode based on the abstract feature extracted in the above-described process (S110).

Figure 2:
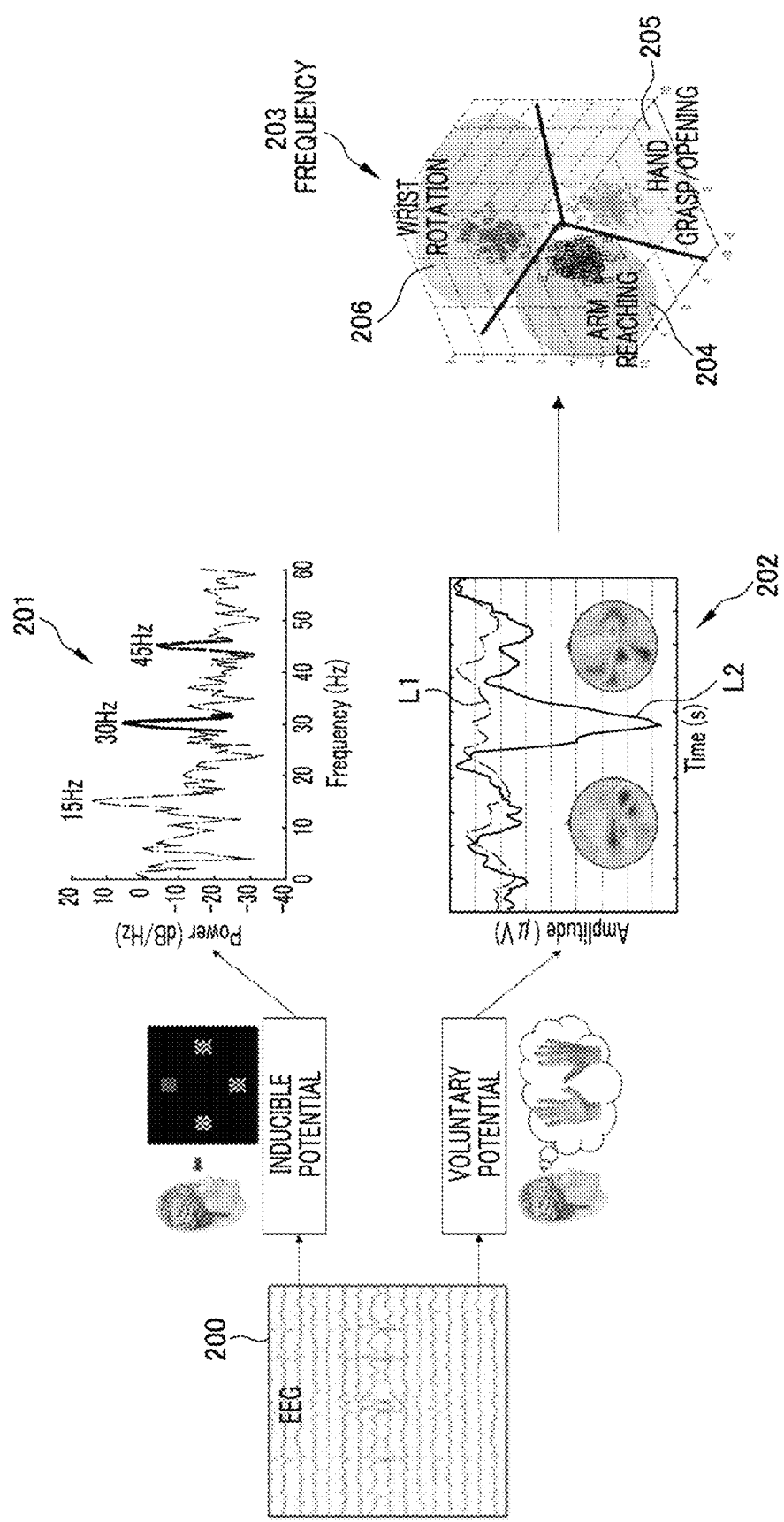
FIG. 2 is a diagram showing a method of determining a control mode in accordance with various embodiments described herein.

FIG. 2 is a diagram showing a method of determining a control mode in accordance with an embodiment of the present disclosure. As shown in FIG. 2, the BCI apparatus 100 extracts a power variance for each frequency band 201 and/or an amplitude variance 202 depending on whether a measured EEG 200 is inducible or voluntary. Herein, a line L1 in the amplitude variance 202 is an EEG pattern in a dormant state and a line L2 is an ERD/ERS pattern expressed during a motion imagery. Further, the term "being inducible" means that the BCI apparatus 100 or another device (not illustrated) obtains a first EEG after visual and/or aural information to induce the user's movement is supplied and the term "being voluntary" means that the BCI apparatus 100 obtains a first EEG in the state where the visual and/or aural information is not supplied.

The BCI apparatus 100 extracts the abstract feature based on the power variance for each frequency band 201 and/or the amplitude variance 202 based on the ERD pattern of the first EEG and determines the control mode accordingly, For example, if a maximum power value of the first EEG corresponds to a first frequency band (e.g., about 15 Hz), the BCI apparatus 100 determines the reaching control mode as a control mode, and if it corresponds to a second frequency band (e.g., about 30 Hz), the BCI apparatus 100 determines the hand grasp/opening control mode as a control mode, and if it corresponds to a third frequency band (e.g., about 45 Hz), the BCI apparatus 100 determines the wrist rotation control mode as a control mode.

Further, if the spatiotemporal feature-concentrated frequency region 203 corresponds to a first region 204, the BCI apparatus 100 determines the reaching control mode as a control mode, and if it corresponds to a second region 205, the BCI apparatus 100 determines the hand grasp/opening control mode as a control mode, and if it corresponds to a third region 206, the BCI apparatus 100 determines the wrist rotation control mode as a control mode.

Referring to FIG. 1 again, the BCI apparatus 100 performs feedback of the control mode determined in the above-described process (S110) to the user (S120). That is, the BCI apparatus 100 may visually and/or audibly notify the user of the determined control mode. For example, the BCI apparatus 100 may notify the user of the determined control mode through a speaker or an LED.

Meanwhile, the above-described processes (S110 to S130) may be performed by an already trained neural network. For example, the BCI apparatus 100 may input the first EEG measured in S100 into the neural network and receive a control mode as a result value. In this case, the neural network may be implemented, including an abstract feature extraction unit for the first EEG and a scalar classifier corresponding to the above-described processes.

Then, the BCI apparatus 100 measures a second EEG for a predetermined period of time (S140) to detect an error generated when selecting the control mode (S150). Herein, the second EEG may be an error-related potential (ErrP) and may be generated when the user determines there is an error. The BCI apparatus 100 may perform filtering of the second EEG in a specific frequency band and then extract a spatiotemporal feature (e.g., frequency amplitude variance value averaged in the direction of time) in the frequency band to determine whether or not the error-related potential exceeds a threshold value. Herein, the threshold is determined based on an average value of error-related potentials measured from an average person in a normal state and can be determined experimentally.

Figure 3:
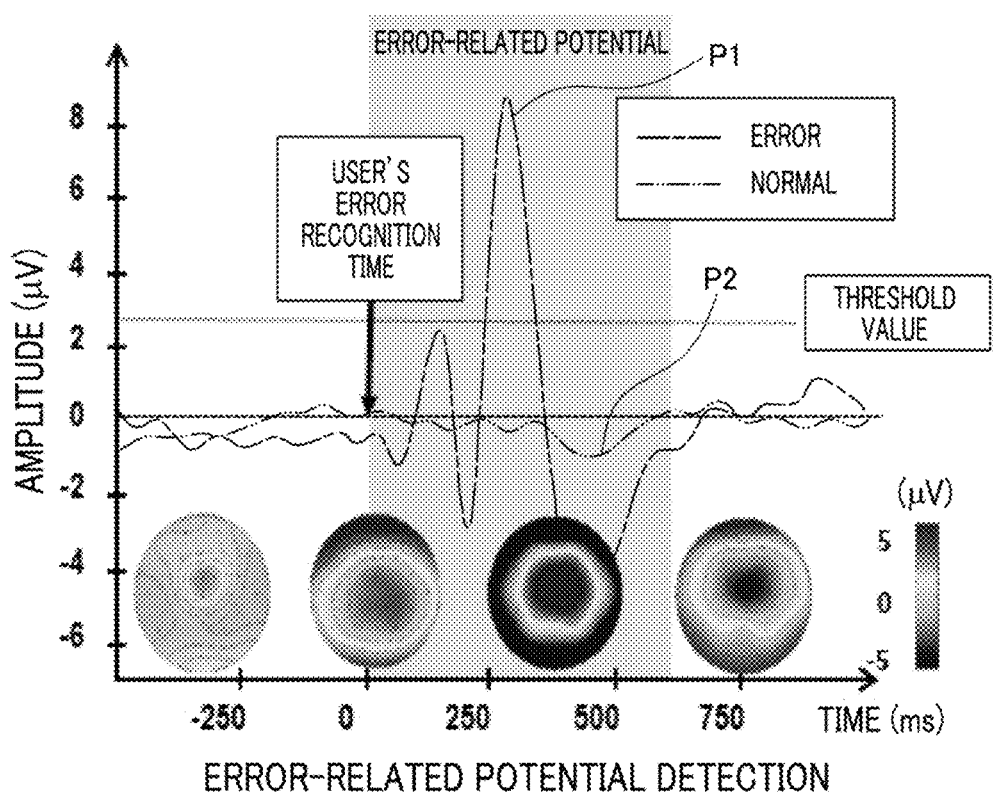
FIG. 3 shows a spatial feature of a second electroencephalogram (EEG) extracted in accordance with various embodiments described herein.

FIG. 3 shows a spatial feature of the second EEG extracted in accordance with an embodiment of the present disclosure. Referring to FIG. 3, it can be seen that the error-related potential does not exceed the threshold value in a normal state (line P2) and converges on "0", but exceeds the threshold value in an error detection state (line P1). As such, the BCI apparatus 100 performs feedback of a control mode to the user and then checks whether or not a control mode is determined correctly by measuring an error-related potential and thus can suppress the robot arm device (not illustrated) from making a motion unintended by the user.

Referring to FIG. 1 again, if the error-related potential exceeds the threshold value in the process S150, the BCI apparatus 100 performs the processes S100 to S140 again. That is, the BCI apparatus 100 may extract an abstract feature of the first EEG again and redetermine a control mode.

However, if the error-related potential does not exceed the threshold value, the BCI apparatus 100 measures a third EEG (S160). Herein, the third EEG is an ERD/ERS signal.

Then, the BCI apparatus 100 may apply different feature extraction methods and different classification methods based on the determined control mode (S170, S180, and S190). Herein, the BCI apparatus 100 extracts features by using all of ERD/ERS signals and generates different control signals based on the respective control modes. For example, the BCI apparatus 100 generates a control signal to stretch a robot arm of the robot arm device (not illustrated) in any one of three-dimensional six directions (front, back, up, down, left, right) from the third EEG corresponding to the reaching control mode. Further, the BCI apparatus 100 generates a control signal to open or bend finger of the robot arm device (not illustrated) from the third EEG corresponding to the hand grasp/opening control mode. Furthermore, the BCI apparatus 100 generates a control signal to rotate a wrist of the robot arm device (not illustrated) to the right or left from the third EEG corresponding to the wrist rotation control mode.

To be specific, in the reaching control mode, the BCI apparatus 100 extracts features in different ways corresponding to the respective control modes based on the ERD/ERS signals (S171, S181, and S191). For example, the BCI apparatus 100 may extract a feature of an ERD/ERS signal in a first frequency region (i.e., about 15 Hz) and then extract a frequency feature by extracting a frequency power value through a signal regression model or extract a spatial feature by using a Laplacian spatial filter. Herein, the frequency region in which the ERD/ERS signal is filtered by the BCI apparatus 100 may be adjusted based on the power variance value for each frequency band analyzed from the first EEG (for example, the first frequency region may be adjusted to from about 15 Hz to about 17 Hz).

Further, in the hand grasp/opening control mode, the BCI apparatus 100 may filter the third EEG in a second frequency region (i.e., about 30 Hz) and then extract a spatiotemporal feature by using a common spatial pattern algorithm or filter the third EEG in a low frequency region (e.g., 30 Hz or less) and then extract a frequency feature.

Furthermore, in the wrist rotation control mode, the BCI apparatus 100 may extract a feature by using spatiotemporal source localization for the third EEG. For example, the BCI apparatus 100 separates the third EEG into multiple signal spaces (e.g., signal spaces and noise spaces) and then extracts a feature of a signal source with the highest contribution to a measured EEG from among multiple signal sources based on base vectors of the signal spaces.

Then, the BCI apparatus 100 performs different feature classification operations corresponding to the respective control modes based on the features extracted in the above-described processes and thus generates control signals corresponding to the respective control modes (S172, S182, and S192). That is, the BCI apparatus 100 performs classification operations by applying the feature extraction methods and classification methods optimized for the respective control modes.

For example, in the reaching control mode, the BCI apparatus 100 determines one of three-dimensional six directions (front, back, up, down, left, right) by applying linear discriminant analysis (LDA), support vector machine (SVM), or the like. Herein, the linear discriminant analysis (LDA) refers to a method of statistically determining characteristics of each feature group and generating a base vector which is easy to be repeatedly segmented. Further, the support vector machine (SVM) refers to a method of generating a non-probabilistic binary linear classification model to determine which category a new feature group belongs to based on a given feature group belonging to any one of two categories. Herein, a result value of the classification model indicates one of the three-dimensional six directions, and the BCI apparatus 100 generates a control signal based on the result value of the classification model.

Further, in the hand grasp/opening control mode, the BCI apparatus 100 determines one of hand grasp and opening motions by applying principal component analysis, independent component analysis, or the like to the extracted feature (i.e., spatiotemporal feature). Herein, the principal component analysis (PCA) refers to a model to linearly convert data into data of a new coordinate system so that axes are placed in such a way that when data of a feature group are mapped to one axis (e.g., time axis), an axis on which the variance thereof is largest is selected as a first coordinate axis, and an axis on which the variance is next largest is selected as a second coordinate axis. Further, the independent component analysis (ICA) refers to a classification model to statistically divide statistically independent non-Gaussian signals into sub-components. A result value of the classification model indicates a hand grasp or opening motion, and the BCI apparatus 100 generates a control signal based on the result value of the classification model.

Further, in the wrist rotation control mode, the BCI apparatus 100 determines a rotation direction (left/right) by applying logistic regression analysis or the like to the extracted feature (i.e., EEG feature). Herein, the logistic regression analysis (LRA) refers to a statistical classification model to analyze the relationship between a dependent variable, i.e., left/right, and an independent variable, i.e., feature group, and predict the dependent variable (i.e., left/right) based on the independent variable. A result value of the classification model indicates a left or right rotation motion, and the BCI apparatus 100 generates a control signal based on the result value of the classification model.

Then, the BCI apparatus 100 supplies the generated control signal to the linked robot arm device (not illustrated).

Figure 4:
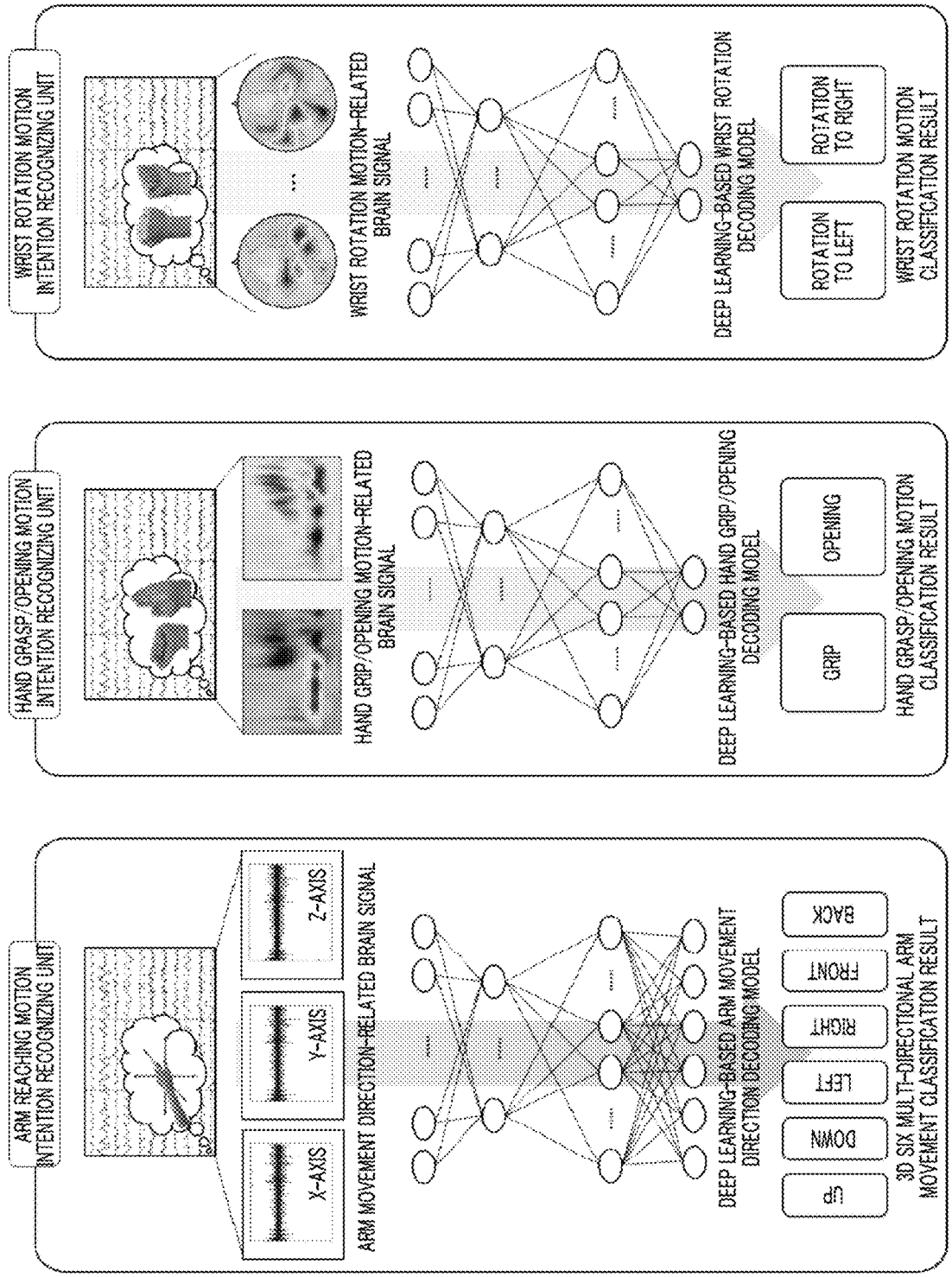
FIG. 4 illustrates a series of processes for generating a control signal from a third EEG by a BCI apparatus in accordance with various embodiments described herein.

FIG. 4 illustrates a series of processes for generating a control signal from a third EEG by the BCI apparatus 100 in accordance with an embodiment of the present disclosure. As illustrated in FIG. 4, the BCI apparatus 100 uses different extraction methods corresponding to the determined control modes, respectively, to extract features from the third EEG and uses different classification methods to output control signals corresponding to the respective control modes.

As such, the BCI apparatus 100 according to the above-described embodiments of the present disclosure extracts an abstract feature of the first EEG to rapidly determine a control mode and checks whether or not a control mode is determined correctly based on an error-related potential and then applies a feature extraction method and classification method optimized for the control mode and thus more accurately generates a control signal corresponding to a motion imagined (or motion intended) by the user.

FIG. 5 illustrates a configuration of the BCI apparatus 100 in accordance with an embodiment of the present disclosure. The BCI apparatus 100 described below is related to the embodiments illustrated in FIG. 1 to FIG. 4. Therefore, detailed descriptions of the BCI apparatus 100 illustrated in FIG. 1 to FIG. 4 may be identically applied to the BCI apparatus 100 illustrated in FIG. 5, even though they are omitted hereinafter.

Referring to FIG. 5, the BCI apparatus 100 includes an EEG measurement device 110, a pre-processing unit 120, a memory 130, and a control unit 140.

The EEG measurement device 110 is configured to measure an electroencephalogram (EEG) of the user under the control of the control unit 140. Herein, the EEG measurement device 110 measures EEGs through multiple channels in contact with multiple brain regions of the user.

The pre-processing unit 120 is configured to perform signal processing corresponding to the measured EEGs. For example, the pre-processing unit 120 may perform noise filtering, frequency filtering, Laplacian spatial filtering, or the like to the measured EEGs.

The memory 130 stores a program that generates a control signal to control a motion of the robot arm device (not illustrated) linked to the BCI apparatus 100. Herein, the memory 130 may collectively refer to a non-volatile storage device that retains information stored therein even when power is not supplied and a volatile storage device that requires power to retain information stored therein.

The control unit 140 includes one or more components configured to control the overall operations of the BCI apparatus 100. Particularly, the control unit 140 may include at least one processor (not illustrated) configured to read the program stored in the memory 130 and execute the program.

To be specific, the control unit 140 extracts an abstract feature form a first EEG measured by the EEG measurement device 110. The first EEG may be an ERD signal, and the abstract feature of the first EEG may be an abstract value as at least one of a frequency feature and a spatiotemporal feature based on an ERD signal. That is, the control unit 140 may extract a frequency or spatiotemporal feature using an ERD pattern of the first EEG extracted through the pre-processing unit 120 and then convert the extracted feature into a scalar value. In this case, the control unit 140 may obtain a maximum power value based on a power variance for each frequency band corresponding to the ERD signal or average a frequency amplitude corresponding to the ERD signal in the direction of time to obtain a frequency region in which spatiotemporal features are concentrated, based on the extracted spatiotemporal feature. However, the present disclosure may not be limited thereto. The control unit 140 may use an already trained classifier to extract the abstract feature of the first EEG.

Then, the control unit 140 is configured to determine one of the reaching control mode, the hand grasp/opening control mode, and the wrist rotation control mode based on the abstract feature of the first EEG.

Then, the control unit 140 may visually and/or audibly notify the user of the determined control mode. To this end, the BCI apparatus 100 may further include a notification device such as a speaker or an LED.

Then, the control unit 140 is configured to compare a threshold with a second EEG (i.e., error-related potential) measured for a predetermined period of time after feedback. If the error-related potential exceeds the threshold value, the control unit 140 repeatedly performs the above-described processes to extract an abstract feature of the first EEG again and redetermine a control mode.

If the error-related potential does not exceed the threshold value, the control unit 140 measures a third EEG. Herein, the third EEG is an ERD/ERS signal, and the control unit 140 performs the following process based on the ERD/ERS signal.

If the reaching control mode is determined as the control mode, the control unit 140 may filter the third EEG in a first frequency region (i.e., about 15 Hz) and then extract a frequency power value of the third EEG through the signal regression model and extract any one of front, back, up, down, left, and right directions as a result value by applying at least one of linear discriminant analysis (LDA), support vector machine (SVM), and the like.

Otherwise, if the hand grasp/opening control mode is determined as the control mode, the control unit 140 may filter the third EEG in a second frequency region and then extract a spatiotemporal feature by using a common spatial pattern algorithm and extracts one of hand grasp and hand opening motions as a result value by applying at least one of principal component analysis and independent component analysis.

If the wrist rotation control mode is determined as the control mode, the control unit 140 may extract a feature by applying spatiotemporal source localization to the third EEG and extract one of left rotation and right rotation as a result value by applying logistic regression analysis.

The control unit 140 generates a control signal to control a motion of the robot arm device (not illustrated) based on the result value extracted in the above-described processes. That is, the control signal may instruct the robot arm device (not illustrated) to make at least one of an reaching motion in any one direction, a hand grasp/opening motion, and a left/right rotation motion of the wrist.

Meanwhile, the generated control signal may be supplied to the robot arm device (not illustrated) through a communication unit (not illustrated). The communication unit (not illustrated) may include one or more components configured to communicate with an external device (e.g., the robot arm device or other devices) under the control of the control unit 140. For example, the communication unit (not illustrated) may be configured using communication wire, Bluetooth, Bluetooth Low Energy (BLE), Infrared Data Association (IrDA), Zigbee, Wi-fi, etc.

The embodiment of the present disclosure can be embodied in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage media. The computer storage media include all volatile/non-volatile and removable/non-removable media embodied by a certain method or technology for storing information such as computer-readable instruction code, a data structure, a program module or other data.

The method and system of the present disclosure have been explained in relation to a specific embodiment, but their components or a part or all of their operations can be embodied by using a computer system having general-purpose hardware architecture.

The above description of the present disclosure is provided for the purpose of illustration, and a person would understand it with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

We claim:

1. A method of generating a control signal to control a robot arm device by a brain-computer interface (BCI) apparatus, comprising:

measuring a first EEG (electroencephalogram) and extracting an abstract feature of the first EEG;

determining one control mode of a reaching control mode, a hand grasp/opening control mode, and a wrist rotation control mode for the robot arm device based on the abstract feature of the first EEG;

performing feedback of the determined control mode to a user;

measuring an error-related potential as a second EEG;

redetermining the control mode by re-extracting an abstract feature of the first EEG when the error-related potential exceeds a threshold value or measuring a third EEG when the error-related potential does not exceed the threshold value;

extracting a result value by applying different feature extraction methods and different classification methods to the third EEG depending on the determined control mode; and supplying a generated control signal based on the result value to the robot arm device wherein the step of extracting a result value includes:

when the control mode is determined as the reaching control mode, filtering the third EEG in a first frequency region and then extracting a frequency power value of the third EEG through a signal regression model and extracting any one of front, back, up, down, left, and right directions as a result value by applying at least one of linear discriminant analysis (LDA) and support vector machine (SVM);

when the control mode is determined as the hand grasp/opening control mode, filtering the third EEG in a second frequency region and then extracting a spatiotemporal feature by using a common spatial pattern algorithm and extracting one of hand grasp and hand opening motions as a result value by applying at least one of principal component analysis and independent component analysis; and when the control mode is determined as the wrist rotation control mode, extracting a feature by applying spatiotemporal source localization to the third EEG and extracting one of left rotation and right rotation as a result value by applying logistic regression analysis.

2. The method of generating a control signal to control a robot arm device by a BCI apparatus of claim 1,
wherein the extracting of the abstract feature of the first EEG includes:
extracting at least one of frequency feature and a spatiotemporal feature based on an event-related desynchronization (ERD) signal of the first EEG; and
converting the extracted frequency feature or the extracted spatiotemporal feature into a scalar value.

3. The method of generating a control signal to control a robot arm device by a BCI apparatus of claim 2,
wherein in the converting of the extracted frequency feature or the extracted spatiotemporal feature into the scalar value, a maximum power value is extracted based on a power variance for each frequency band of the first EEG, or a feature region output through an already trained classifier is obtained based on an amplitude variance averaged in the direction of time of the first EEG.

4. The method of generating a control signal to control a robot arm device by a BCI apparatus of claim 1,
wherein the first EEG is filtered in a frequency band of from 5 Hz to 50 Hz.

5. A brain-computer interface (BCI) apparatus, comprising:
an electroencephalogram (EEG) measurement device that measures an EEG;
a memory that stores a program with which the BCI apparatus generates a control signal to control a motion of a robot arm device linked to the BCI apparatus; and
a control unit that executes the program stored in the memory,
wherein upon execution of the program, the control unit extracts an abstract feature of a first EEG based on the first EEG measured by the EEG measurement device, determines one control mode of a reaching control mode, a hand grasp/opening control mode, and a wrist rotation control mode for the robot arm device based on the abstract feature, and the control unit performs feedback of the determined control mode to a user and compares an error-related potential measured as a second EEG by the EEG measurement device with a threshold value, and the control unit redetermines the control mode by remeasuring the first EEG when the error-related potential exceeds the threshold value, or the control unit extracts a result value by applying different feature extraction methods and different classification methods to a third EEG measured by the EEG measurement device depending on the determined control mode when the error-related potential does not exceed the threshold value and supplies a control signal generated based on the result value to the robot arm device, wherein when the control mode is determined as the reaching control mode, the control unit filters the third EEG in a first frequency region and then extracts a frequency power value of the third EEG through a signal regression model, and extracts any one of front, back, up, down, left, and right directions as a result value by applying at least one of linear discriminant analysis (LDA) and support vector machine (SVM);

when the control mode is determined as the hand grasp/opening control mode, the control unit filters the third EEG in a second frequency region and then extracts a spatiotemporal feature by using a common spatial pattern algorithm, and extracts one of hand grasp and hand opening motions as a result value by applying at least one of principal component analysis and independent component analysis; and when the control mode is determined as the wrist rotation control mode, the control unit extracts a feature by applying spatiotemporal source localization to the third EEG, and extracts one of left rotation and right rotation as a result value by applying logistic regression analysis.

6. A non-transitory computer-readable storage medium that stores a program configured to implement the method of claim 1 on a computer.

* * * * *